(12) United States Patent
Opitz et al.

(10) Patent No.: US 12,412,653 B2
(45) Date of Patent: Sep. 9, 2025

(54) SYSTEM AND METHOD FOR VISUAL ANALYSIS OF EVENT SEQUENCES

(71) Applicant: ABBYY Development Inc., Dover, DE (US)

(72) Inventors: Scott Opitz, Media, PA (US); Alex Elkin, Acton, MA (US)

(73) Assignee: ABBYY Development Inc., Dover, DE (US)

( * ) Notice: Subject to any disclaimer, the term of this patent is extended or adjusted under 35 U.S.C. 154(b) by 442 days.

(21) Appl. No.: 17/353,645

(22) Filed: Jun. 21, 2021

(65) Prior Publication Data

US 2021/0313056 A1 Oct. 7, 2021

Related U.S. Application Data

(63) Continuation of application No. 15/650,418, filed on Jul. 14, 2017, now Pat. No. 11,043,298.

(60) Provisional application No. 62/363,377, filed on Jul. 18, 2016.

(51) Int. Cl.
| | |
|---|---|
| *G16H 40/20* | (2018.01) |
| *G06F 16/2458* | (2019.01) |
| *G06F 16/26* | (2019.01) |
| *G06F 16/358* | (2025.01) |
| *G06F 40/56* | (2020.01) |
| *G06N 5/025* | (2023.01) |
| *G16H 10/60* | (2018.01) |
| *G06N 7/01* | (2023.01) |
| *G06N 20/00* | (2019.01) |
| *G16H 10/20* | (2018.01) |

(52) U.S. Cl.
CPC ......... *G16H 40/20* (2018.01); *G06F 16/2474* (2019.01); *G06F 16/26* (2019.01); *G06F 16/358* (2019.01); *G06F 40/56* (2020.01); *G06N 5/025* (2013.01); *G16H 10/60* (2018.01); *G06N 7/01* (2023.01); *G06N 20/00* (2019.01); *G16H 10/20* (2018.01)

(58) Field of Classification Search
None
See application file for complete search history.

(56) References Cited

U.S. PATENT DOCUMENTS

| | | | |
|---|---|---|---|
| 10,146,609 B1 * | 12/2018 | Leverich | G06F 11/079 |
| 10,156,963 B2 | 12/2018 | Patel et al. | |
| 11,195,213 B2 * | 12/2021 | Dastmalchi | G06Q 40/08 |

(Continued)

FOREIGN PATENT DOCUMENTS

| | | | | |
|---|---|---|---|---|
| AU | 2016204072 A1 * | 1/2017 | | G06F 16/254 |

OTHER PUBLICATIONS

Sherrick, An Introduction to Graphical User Interfaces and Their Use by CITIS, U.S. Department of Commerce, Technology Administration, National Institute of Standards and Technology, Jul. 1992; Total pp. 34 (Year: 1992).*

*Primary Examiner* — Alan Chen
(74) *Attorney, Agent, or Firm* — Lowenstein Sandler LLP

(57) ABSTRACT

Techniques are disclosed for creating event sequences from event data and then providing a visual analysis of event sequences. Event-related data for a set of event sequences is analyzed, and event sequences are grouped. Sequence metrics are calculated for the event sequences, and a user interface is provided to display a visual representation of the set of event sequences and the sequence metrics for the set of event sequences.

20 Claims, 9 Drawing Sheets

(56) References Cited

U.S. PATENT DOCUMENTS

| | | | |
|---|---|---|---|
| 2010/0017359 A1* | 1/2010 | Kiernan | G06Q 10/10 |
| | | | 706/58 |
| 2011/0029485 A1 | 2/2011 | Park et al. | |
| 2011/0202483 A1 | 8/2011 | Bergman | |
| 2012/0137367 A1* | 5/2012 | Dupont | G06F 21/00 |
| | | | 726/25 |
| 2012/0198317 A1* | 8/2012 | Eppolito | G11B 27/034 |
| | | | 715/202 |
| 2014/0143724 A1* | 5/2014 | Picard | G06T 11/206 |
| | | | 715/828 |
| 2015/0295778 A1 | 10/2015 | Hsiao et al. | |
| 2016/0027278 A1* | 1/2016 | McIntosh | G08B 21/0423 |
| | | | 715/741 |
| 2017/0048264 A1 | 2/2017 | Chauhan et al. | |
| 2017/0220672 A1 | 8/2017 | Sainani et al. | |
| 2017/0300755 A1 | 10/2017 | Bose et al. | |

\* cited by examiner

600 ↘

> SET METRICS:
>
> NUMBER OF SEQUENCES: 2
>
> DURATION: FROM 2 HOURS 32 MINUTES TO 2 HOURS 35 MINUTES
>
> TIME GAP: 48 MINUTES TO 2 HOURS 15 MINUTES

FIG. 6

SYSTEM AND METHOD FOR VISUAL ANALYSIS OF EVENT SEQUENCES

CROSS REFERENCE TO RELATED PATENT APPLICATIONS

This application is a continuation application of U.S. application Ser. No. 15/650,418, filed Jul. 14, 2017, which claims priority to U.S. Provisional Patent Application No. 62/363,377, filed Jul. 18, 2016, and entitled "System and Method for Visual Analysis of Event Sequences," which is hereby incorporated by reference in its entirety.

FIELD OF THE INVENTION

The present invention relates generally to visually analyzing event sequences. More particularly, the present invention is directed to a system and method for providing a visual analysis of large and diverse sets of event sequences by calculating and displaying sequence-specific metrics for an event set, displaying a representative sample of the set, and allowing end users to reduce the set based on the values of the metrics.

BACKGROUND OF THE INVENTION

Many business processes, whether human-driven, automated or a combination thereof, comprise multiple events happening over a period of time. An event, as described herein, is a computer-recorded fact that a particular activity happened at a particular time as related to a particular object. The events could be organized in sequences based on the time when they occur and the object to which they are related. For example, if the object is a patient in a hospital, her sequence includes all events that occurred to this patient. In order to understand the operation of a business process, it is desirable to see the sequences of events and manipulate them in order to focus on particular phenomena of interest.

In this regard, existing analytical tools could be broken onto as general business intelligence, process mining, and sequence analysis categories. General business intelligence tools analyze the relational data consisting of records and field or rows and columns. Such tools are limited in that they do not provide visual interfaces and functionality to visualize and analyze the sequences of records. Additionally, process mining tools reverse-engineer the sequences of events into the process schema in the form of a business process model and notation (BPMN) or similar notations. While this task could be useful in cases where the business does have the underlying process schema, the task of discovering the common denominator for all sequences is different from understanding the variety and peculiarities of the actual sequences. Further, existing sequence analysis tools are designed primarily for the field life sciences, specifically—the analysis of the biological molecules such as DNA Thus, existing sequence analysis tools do not incorporate the concept of time between events. Also, because of a very large number of elements in a single sequence, these tools rely on mathematical algorithms rather than a visual analysis to discover the patterns and deviations.

BRIEF DESCRIPTION OF THE DRAWINGS

The detailed description is described with reference to the accompanying figures, in which the left-most digit(s) of a reference number identifies the figure in which the reference number first appears. The use of the same reference numbers in different figures indicates similar or identical items.

FIGS. 3 through 6 are exemplary diagrams showing how events are processed, according to one embodiment of the present invention.

DETAILED DESCRIPTION OF THE INVENTION

This disclosure is directed to techniques for providing a visual analysis of event sequences using an event sequencing application or tool. Some embodiments of the techniques include receiving event-related data from one or more data sources for a set of event sequences, converting the event-related data associated into event sequences in the set of event sequences, calculating sequence-specific metrics for the event sequences in the set, displaying a representative sample of the event sequences and the calculated metrics on a user interface, receiving a filter selection from the user interface to generate a subset of event sequences, re-calculating sequence-specific metrics for the subset of event sequences, and displaying a visual representation of the subset of event sequences and the recalculated metrics on the user interface.

In various embodiments, the user interface is configured to enable an end user to alter the visual representation of the representative sample of event sequences of the set of event sequences. Without limitation, the configuration options for altering the visual representation include sorting of the sequences based on the metric values or number of occurrences of the specific events, color-coding and/or applying or assigning images or icons to highlight one or more events, hiding one or more events from the sequences, replacing one or more events, and/or so forth.

Additionally, the event sequencing application can use machine learning based algorithms to automatically group event sequences within a set and order the event sequences based at least in part on predetermined criteria. The techniques described herein may be implemented in a number of ways. Example implementations are provided below with reference to the following figures.

Example Architecture

Figure 1:
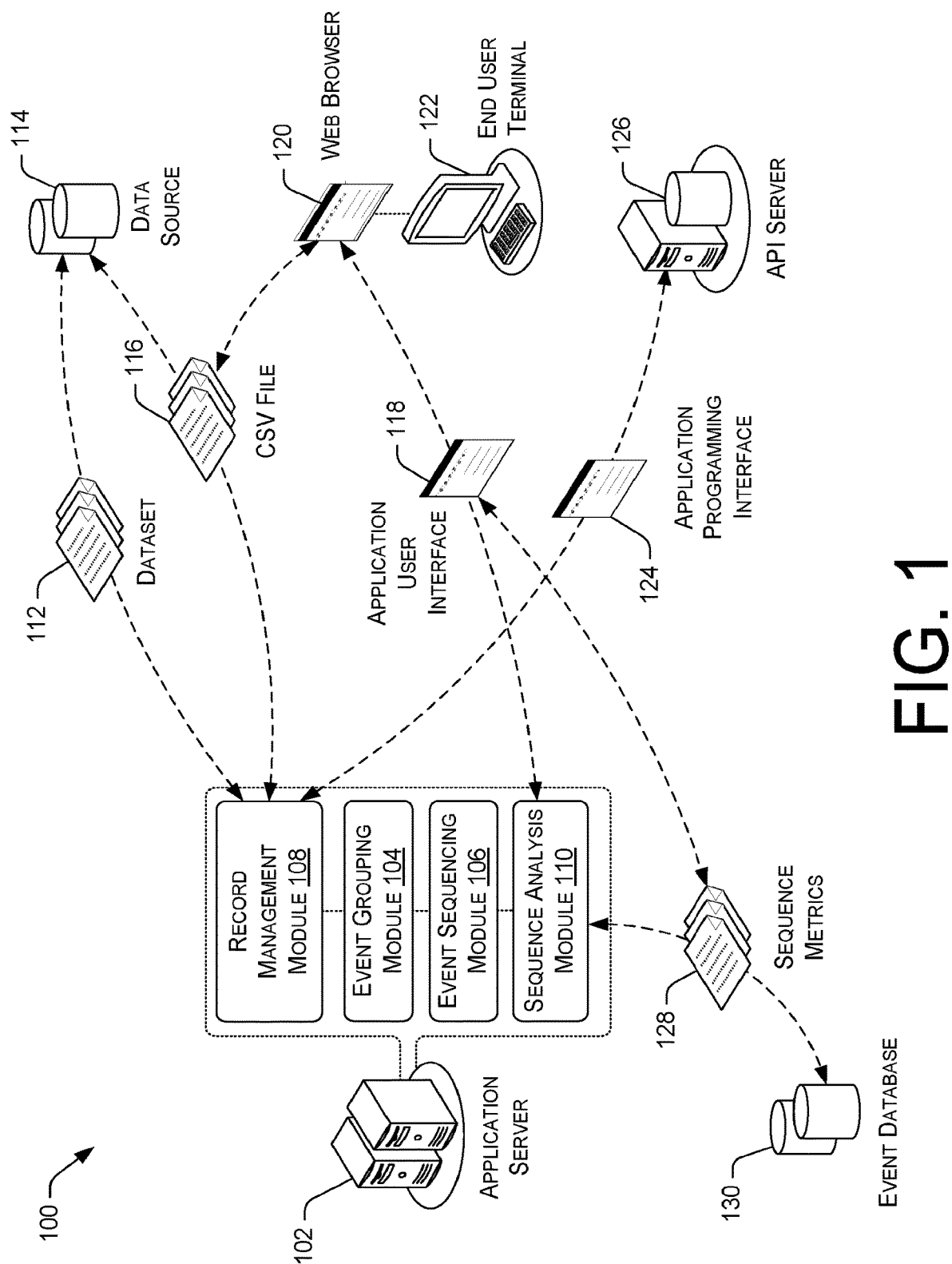
FIG. 1 shows an exemplary architecture for a visual analysis of event sequences.

FIG. 1 illustrates example architecture for providing a visual analysis of event sequences. In one embodiment, the system 100 comprises a network-enabled (i.e., for connection to the Internet, LAN, etc.) computer system, for example, an end user terminal 122 that is operated by an end user. In various embodiments, the end user terminal 122 can include general-purpose computers, mobile handsets, smartphones, tablet computers, personal digital assistants (PDAs), smart watches, and/or other electronic devices. The end user terminal 122 can access an event sequencing application using a web browser 120, wherein the application comprises an application user interface 118 and can reside at least in part on the end user terminal 122, depending upon the embodiment. In various embodiments, the application can be executed in a web browser 120 and is configured to read various data files and transmit the content of the data files to and from various components of the system 100. The event sequencing application comprises a record management module 108, an event grouping module 104, an event sequencing module 106, and a sequence analysis module 110.

The event sequencing application can execute on one or more computing devices in the system 100, such as an application server 102. The application server 102 can be distributed processing computing devices that are scalable according to workload demand. The application server 102 can include general-purpose computers, such as desktop computers, tablet computers, laptop computers, servers, or other electronic devices that are capable of receive inputs, process the inputs, and generate output data. In still other embodiments, the one or more application servers 102 (i.e., computing devices) may be virtual computing devices in the form of computing devices, such as virtual machines and software containers. The application server 102 may store data in a distributed storage system, in which data may be stored for long periods of time and replicated to guarantee reliability. Accordingly, the application server 102 may provide data and processing redundancy, in which data processing and data storage may be scaled in response to demand. Further, in a networked deployment, new application servers 102 may be added on the fly without affecting the operational integrity of the event sequencing application.

The record management module 108 is configured to receive event-related data from various data sources. Event-related data comprises various information associated with one or more events, including, without limitation, event description, individuals, groups, and/or entities associated with an event, event location, timestamp for each event (e.g., onset, duration, etc.), event attribute or event feature, stimulus condition, recording session number, and/or so forth. The record management module 108 can request, receive, deliver, and manage event-related data. In some embodiments, the record management module 108 receives data files 116 in various file formats (e.g., CSV file) comprising event-related data uploaded onto, for example, a website, via the web browser 120 from the end user terminal 122. In this regard, data files can originate from a local memory unit of the end user terminal 122 or imported from a file hosting service, a document management and storage system, a local and/or private communications network, a cloud-based database service, and/or so forth. Additionally, the record management module 108 can receive one or more datasets 112 comprising one or more sets of event-related data from various data sources 114, which can include third party data sources.

To request event-related data, the record management module 108 sends a database query to a data source 114 or another database, such as an event database 130. In some embodiments, the data source 114 or another database can present a list of parameters from which the record management module 108 can select in order to pose a query. Alternatively, the record management module 108 can present query by example (QBE) or provide query language. In some embodiments, the record management module 108 can include a workflow scheduler that periodically checks for and retrieves newly available event-related data from the data source 114 or another database. The workflow scheduler may handle the extraction and the handling of the event-related data based on configurable policies. For example, a configurable policy may specify the source data location, frequency of data retrieval, data retention period, and data disposal following an expiration of the data retention period. Upon receiving a database query, the data source 114 or the database generates a report comprising event-related data based at least in part on the query to the data source 114 or another database. The results of the query are interpreted as the event records and transmitted to the event sequencing application executed on the application server 102.

In some embodiments, event-related data are derived or generated via a third-party application programming interface (API) 124 such as a web service, for example, a service or a system similar to Salesforce.com™ or other customer relationship management (CRM) platforms supported by an API server 126. In this regard, an end user, at the end user terminal 122, can request event-related data by specifying the third party source of the records (e.g., a web service), credentials for authentication and authorization (e.g., login information for a web service), and/or other necessary information to access the data using the application user interface 118. Upon receiving a request for event-related data from a third party API, the event sequencing application is configured to establish a connection to the third party source of the data, using the information supplied by the end user, and obtain the data in the form of computer transmission (e.g., XML, JSON, etc.).

The event grouping module 104 processes event-related data managed via the record management module 108 in order to organize, group, and/or categorize event sequences derived from the event-related data. In this regard, the event group module 104 analyzes event description, individuals, groups, and/or entities associated with an event, event location, timestamp for each event (e.g., onset, duration, etc.), event attribute or event feature, stimulus condition, recording session number, and/or other information associated with each event sequence. Thereafter, each event sequence is assigned a group identifier based at least in part on event grouping criteria, parameters, or particular information associated with each event sequence. For example, the event grouping module 104 can group events based on event location. In this regard, each event sequence associated with a first location can be assigned to Group A, and each event sequence associated with a second location can be assigned to Group B. In another example, the event grouping module 104 can group events based on individuals associated with an event sequence. In this regard, each event sequence associated with individual A can be assigned to Group I and each event sequence associated with individual B can be assigned to Group 2. In various embodiments, an end user can customize, modify, specify, or adjust event grouping criteria or parameters at the end user terminal 122 via the application user interface 118.

The event sequencing module 106 analyzes timestamp associated with each event sequence in order to organize or sort event sequences in a set of event sequences in a chronological or reverse chronological order. In this way, the event sequencing module 106 can provide a timeline of events in a set of event sequences. In various embodiments, the event sequencing module 106 is configured to determine a start time and an end time for an event by identifying the first event and the last event in a set of event sequences. Additionally, the event sequencing module 106 can be configured to calculate the distribution of first and last events in the sequences, duration of each event sequence, total time lapsed over the entire event, time gap between consecutive events, and/or so forth. In this way, the event sequencing module 106 can order event sequences based on the time duration (e.g., shortest duration to the longest duration and vice versa), the time gap between consecutive events (e.g., shortest time gap to the longest time gap and vice versa), and/or so forth.

The sequence analysis module 110 is configured to calculate various sequence metrics 128 associated with a set of event sequences, wherein the sequence metrics 128 can be stored in an event database 130. In various embodiments, the sequence metrics 128 comprise a number of events per event sequence within a set of event sequences, a number of individuals, groups, and/or entities associated with an event, a number of event locations, a number of event attributes or event features, dataset-specific metrics based on the values of the event attributes, a number of stimulus conditions, recording session numbers, duration and time gaps for event sequences, and/or so forth. The attribute based metrics 128 can vary depending upon the embodiment. For example, the sequence metrics 128 for marketing operation can comprise average cost per session, average events per session, average events per user, average order value, average user duration, cost of acquisition, customer lifetime value, effective revenue share, non-bounce rate, non-bounces, non-landing (web)pages page views, (web)pages per user, publisher revenue per user, return on investment (ROI), revenue, revenue after refunds, revenue per session, revenue per user, session per clicks, sessions per user, total events or total number of unique events, transactions per user, user e-commerce conversion rate, and/or so forth.

In various embodiments, the sequence analysis module 110 can determine the number of events within the set of event sequences, the number of individuals, groups, and/or entities associated with an event, the number of event locations, the number of event attributes or event features, the number of stimulus conditions, recording session numbers, and/or so forth. Additionally, the sequence analysis module 110 can also calculate duration and time gaps for event sequences based at least partially on the timestamp associated with each event. Thus, the sequence analysis module 110 can provide data for event metrics. Further, the sequence analysis module 110 can calculate sequence metrics 128 based on sequence metrics criteria or parameters as specified by an end user at the end user terminal 122. For example, the sequence analysis module 110 can receive a selection, via the application user interface 118, to calculate a specific sequence metric such as a number of events in a set of event sequences or in a group within the set of event sequences.

In various embodiments, the sequence analysis module 110 is configured to display sequence metrics 128 associated with a set of event sequences via the application user interface 118. Additionally, the sequence analysis module 110 is configured to generate a visual representation of the event sequences within the set to display on the application user interface 118. The application user interface 118 enables an end user to interact with one or more components of the present system 100, including the record management module 108, the event grouping module 104, the event sequencing module 106, and the sequence analysis module 110 of the event sequencing application. The application user interface 118 can display the visual representation of the event sequences in a timeline, roadmap, chart, graph, workflow, histogram, and/or so forth.

The event database 130 can comprise a standalone database or a part of a data store that comprises software utilities and additional databases that facilitate the acquisition, processing, storage, reporting, and analysis of event-related data from multiple data sources. The event database 130 may store data across multiple virtual data storage clusters with redundancy, so that the data may be optimized for quick access. For example, event database 130 can be partially replicated on the application server 102. The data store component may provide a data access API that provides access to one or more databases and/or data sources. The data access API may also be used by custom analytic engines and/or other third party tools to access the data in the different databases. The data store component may access the multiple data sources via a network. The network may be a local area network (LAN), a larger network such as a wide area network (WAN), or a collection of networks, such as the Internet. The data store component may use multiple connectors in the form of applications, APIs, protocols, and services, to support connectivity with data sources and data stores. These connectors may include FTP/SFTP, HTTP/HTTPS, and/or so forth.

Example Computing Device Components

Figure 2:
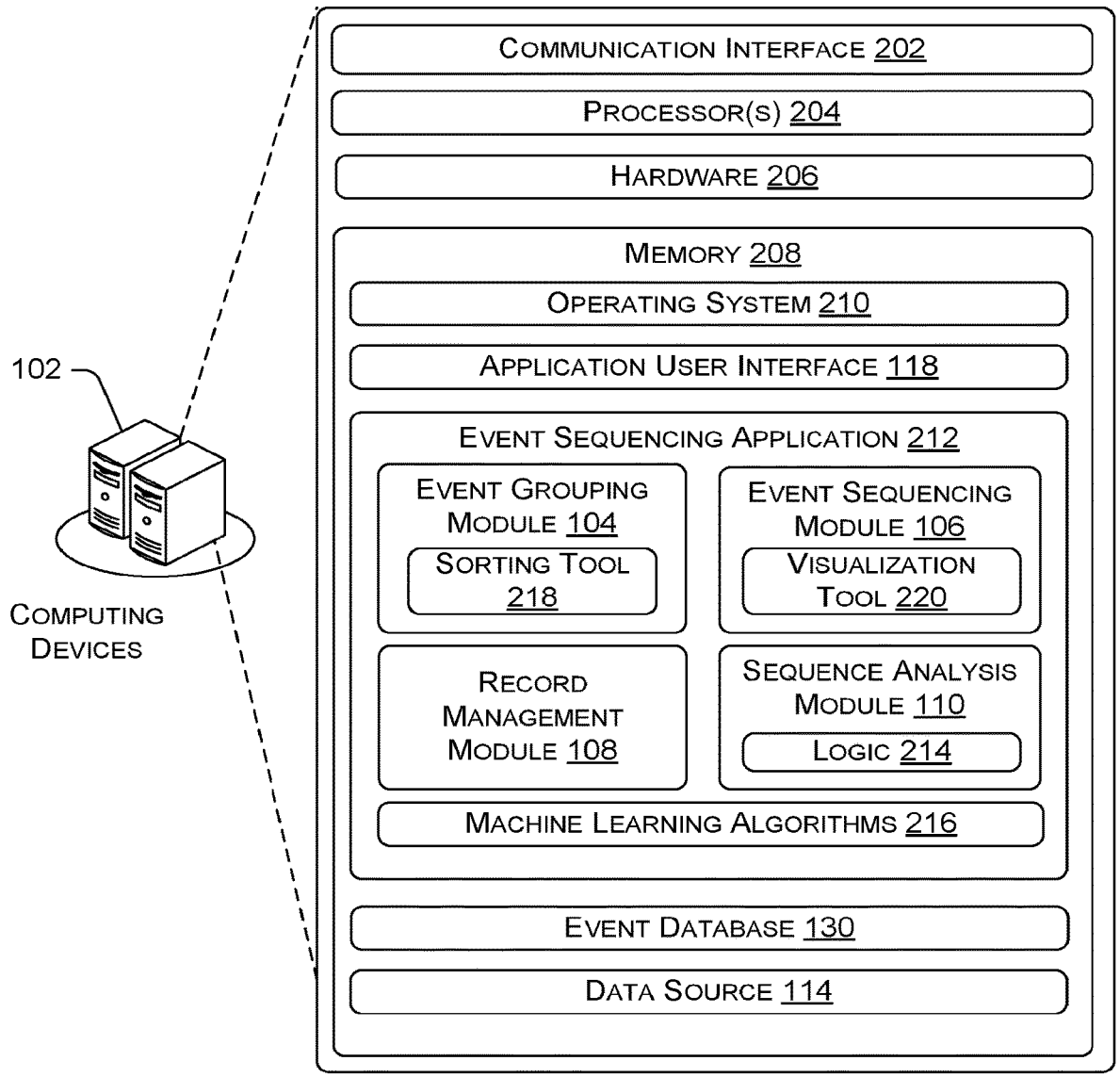
FIG. 2 is a block diagram showing various components of one or more illustrative computing devices that implement a visual analysis of event sequences.

FIG. 2 is a block diagram showing various components of one or more illustrative computing devices 102 (e.g., an application server) that implement an event sequencing application that provides a visual analysis of event sequences. The number of computing devices 102 may be scaled up and down by a distributed processing control algorithm based on the data processing demands of the event sequencing application, data store, and/or other components in the system. For example, during peak performance data processing times, the number of computing devices 102 that are executing event sequence analysis functionalities may be scaled up on the fly based on processing demand. However, once the processing demand drops, the number of computing devices 102 that are executing the event sequence analysis functionalities may be reduced on the fly. Such scaling up and scaling down of the number of computing devices 102 may be repeated based on processing demand.

The computing devices 102 may include a communication interface 202, one or more processors 204, hardware 206, and a memory unit 208. The communication interface 202 may include wireless and/or wired communication components that enable the devices to transmit data to and receive data from other networked devices. The hardware 206 may include additional hardware interface, data communication, or data storage hardware. For example, the hardware interfaces may include a data output device (e.g., visual display, audio speakers), and one or more data input devices. The data input devices may include but are not limited to, combinations of one or more of keypads, keyboards, mouse devices, touch screens that accept gestures, microphones, voice or speech recognition devices, and any other suitable devices.

The memory unit 208 may be implemented using computer-readable media, such as computer storage media. Computer-readable media includes, at least, two types of computer-readable media, namely computer storage media and communications media. Computer storage media includes volatile and non-volatile, removable and non-removable media implemented in any method or technology for storage of information such as computer-readable instructions, data structures, program modules, code segments, or other data. Computer storage media includes, but is not limited to, RAM, ROM, EEPROM, flash memory or other memory technology, CD-ROM, digital versatile disks (DVD), high-definition multimedia/data storage disks, or other optical storage, magnetic cassettes, magnetic tape, magnetic disk storage or other magnetic storage devices, or any other non-transmission medium that can be used to store information for access by a computing device. In contrast, communication media may embody computer-readable instructions, data structures, program modules, code segments, or other data in a modulated data signal, such as a carrier wave, or another transmission mechanism.

The processors 204 and the memory unit 208 of the computing devices 102 may implement an operating system 210. In turn, the operating system 210 may provide an execution environment for the event sequencing application 212, the application user interface 118, the event database 130, and/or the data source 114. The operating system 210 may include components that enable the computing devices 102 to receive and transmit data via various interfaces (e.g., user controls, communication interface, and/or memory input/output devices), as well as process data using the processors 204 to generate output. The operating system 210 may include a presentation component that presents the output (e.g., display the data on an electronic display, store the data in memory, transmit the data to another electronic device, etc.). Additionally, the operating system 210 may include other components that perform various additional functions generally associated with an operating system.

The event sequencing application 212 comprises the event grouping module 104, the event sequencing module 106, the record management module 108, and the sequence analysis module 110, wherein each of the modules can interact with an end user via the application user interface 118 at an end user terminal. The record management module 108 collects, stores, and manages event-related data, which comprise event sequences and all related data and metadata associated therewith. Additionally, the record management module 108 can provide a request for event-related data from the event database 130 or another data source 114, which may or may not reside on the computing devices 102. In various embodiments, the record management module 108 may use data adaptors to retrieve data from the structured or unstructured databases of the data sources described above (e.g., company database, module database, user database, developer database, host database). Because the structured databases can provide data that are accessible via simple data retrieval algorithms, the record management module 108 can use data-agnostic data adaptors to access the data sources without taking into consideration the underlying content of the data. Further, changes to the data content in each data source do not affect the functionality of the corresponding data-agnostic data adaptors. Alternatively, the record management module 108 may use database-specific data adaptors to access structured databases.

In various embodiments, the record management module 108 implements adaptor-specific logics to decode the format of various data from respective data sources so that it is not limited to processing certain types of data format. Accordingly, event-related data from one data source may be fed into other data sources, modules (e.g., record management module 108, event sequencing module 106, event grouping module 104, sequence analysis module 110), and/or components of the present system for analysis and storage. For example, event-related data can be fed into the event grouping module 104 for organizing event-related data by sorting event sequences associated with the event-related data into groups based on predetermined event grouping criteria.

The event grouping module 104 analyzes event-related data in order to identify event description, individuals, groups, and/or entities associated with an event, event location, timestamp for each event (e.g., onset, duration, etc.), event attribute or event feature, stimulus condition, recording session number, and/or other categories of information associated with each event sequence in the event-related data. The event sequences can be grouped manually or automatically using a sorting tool 218 that is accessible from the application user interface 118. In various embodiments, the sorting tool 218 can provide a list of event grouping criteria from which an end user can select via the application user interface 118. For example, the event grouping criteria can comprise grouping event sequences by event description, individuals, groups, and/or entities associated with each event sequence, event location, time, duration, and/or time gap of each event sequence, event attribute or event feature, stimulus condition, recording session, and/or other such information. Upon receiving one or more selection of the event grouping criteria, the sorting tool 218 triggers the event grouping module 104 to assign a group identifier to each event sequence within a set of event sequences based at least in part on the user's selection of the event grouping criteria. For instance, an end user can select and specify an event attribute as an event grouping criteria, and the sorting tool 218, upon receiving the end user's selection, can trigger the event grouping module to group event sequences based on the event attribute within a set of event sequences by the event attribute.

In various embodiments, more than one event grouping criteria can be selected using the sorting tool 218. In this regard, the sorting tool 218 is configured to trigger the event grouping module 104 to assign a group identifier for each event grouping criteria or assign a group identifier for each event sequence meeting one or more of the event grouping criteria. For example, an end user can select an event location, an individual associated with an event sequence, and time duration for an event sequence as event grouping criteria. In this regard, the event grouping module 104 can assign a group identifier for each of the event location (e.g., Group A), individuals associated with an event sequence (e.g., Group B), and time duration for an event sequence (e.g., Group C). Alternatively, the end user can specify, via the sorting tool 218, to group the event location and individuals associated with an event sequence together and the time duration for an event sequence by itself In this regard, the event grouping module 104 can assign a group identifier for each of the event location and individuals associated with an event sequence (e.g., Group A) and time duration for an event sequence (e.g., Group B).

In some embodiments, the event grouping module 104 groups events based on the probability of the events to occur in the same event sequence. For example, events N and M belong to the same group if:

$P(N/M) > Q$ and $P(M/N) > Q$;

where $P(X/Y)$ is the probability of event Y occurring in a sequence where event X exists, and Q is the probability threshold from the interval (0, 1). Thus, if a first event associated with a particular location is likely to occur in the same event sequence as a second event associated with a particular individual, the first event and the second event can be grouped together. Some embodiments of the event grouping module 104 can implement one or more supervised or unsupervised machine learning algorithms and at least one trained machine learning model or other data to draw inferences regarding different event grouping criteria. Based on the inferences and/or end user preferences, the event grouping module 104 can automatically assign group identifiers to event sequences in order to organize the event sequences by a group.

The event sequencing module 106 is configured to sort event sequences in a set of event sequences derived from event-related data in a chronological order. In this regard, the event sequencing module 106 can refer to the timestamp associated with each event sequence. Additionally, the event sequencing module 106 can organize events sequences in other sequential or consecutive order. In various embodiments, the event sequencing module 106 is also configured to sort event sequences based on metric values associated with each event sequence in a set or number of occurrences of the specific events using a visualization tool 220 that is accessible from the application user interface 118. For instance, the visualization tool 220 provides a list of visualization options from which an end user can select via the application interface 118. In this regard, the end user can utilize the visualization tool 220 in order to filter visuals for event sequences based on time gaps, number of events, duration, and/or other sequence metrics. Additionally, the visualization tool 220 comprises a color-coding feature or other animation features for applying and/or assigning images or icons to highlight one or more events, hiding one or more events from the sequences, replacing one or more events in a set of event sequences, and/or so forth. For example, the end user can select a color-coding feature to assign different colors to a visual representation of certain event sequences (e.g., event groups) in order to more easily identify those event sequences on the application user interface 118.

The sequence analysis module 110 can implement logic 214 in order to calculate and provide sequence metrics for event sequences in a set. The type of sequence metrics can vary depending upon the embodiment. For example, the sequence metrics can relate to marketing, patient triage, social events, social networking, and/or so forth. In various embodiments, the sequence metrics 128 can comprise quantitative data such as a number of events within a set of event sequences, a number of individuals, groups, and/or entities associated with an event, a number of event locations, a number of event attributes or event features, a number of stimulus conditions, recording session numbers, duration and time gaps for event sequences, and/or so forth. Additionally, the sequence metrics can comprise qualitative data such as the location of the events, name or identity of individuals, groups, and/or entities associated with an event, event attributes or event features, stimulus conditions, patterns, narratives, event structures, and/or so forth. The sequence analysis module 110 can implement one or more supervised or unsupervised machine learning algorithms in order to draw inferences regarding qualitative and/or quantitative data.

To calculate or provide sequence metrics, the sequence analysis module 110 obtains a set of event sequences from the record management module 108, wherein the set of event sequences can comprise an original set of events (i.e., all of the event sequences from the start time and the end time for an event) or a representative subset of sequences within the set of event sequences. The set of event sequences can be organized in a list in a sequential order and/or in groups (e.g., via the event grouping module 104 and/or the event sequencing module 106) so as to allow the sequence analysis module 110 to count, for example, a number of events within the set of event sequences. Additionally, the sequence analysis module 110 can identify the earliest event and the latest event from the list to determine the difference of time based on the timestamps associated with the earliest event and the latest event, thereby calculating the duration of the set of event sequences. Further, the sequence analysis module 110 can calculate the time gap between each of the consecutive events in the list by determining the difference between the end time of the first event sequence and the start time of the second event sequence following the first event sequence, then the end time of the second event sequence and the start time of the third event sequence following the second event sequence, and so on.

The event sequencing application 212 can utilize at least one trained machine learning model to analyze event-related data and metadata to automatically group different events in a set of event sequences. The machine learning model can be augmented as needed by adding additional training datasets and/or training results from one or more machine learning algorithms 216 based on feedback regarding the accuracy of the grouping predictions and event ordering.

Using the sorting tool 218, the event sequences in the original set of event sequences or a representative subset of sequences within the set of event sequences can be filtered, regrouped, and/or reorganized based on calculated metrics and/or other criteria and parameters. Without limitation, the filtering criteria and parameters can include event description, individuals, groups, and/or entities associated with an event, event location, timestamp for each event (e.g., onset, duration, etc.), event attribute or event feature, stimulus condition, recording session number, and/or so other event-related information. The sorting tool 218 of the event grouping module 104 can receive a filter selection based on the calculated metrics or filtering criteria, from the end user, to filter the original set of event sequences or a representative subset of sequences and generate a new representative subset or a new representative sample of event sequences. The sequence analysis module 110 can recalculate the sequence metrics associated with the new representative subset or the new representative sample of event sequences.

Upon calculating sequence metrics, the sequence analysis module 110 is configured to display the calculated metrics on the application user interface 118. Additionally, the sequence analysis module 110 can generate a visual representation of the event sequences correlating to the calculated metrics for display on the application user interface 118. The visual representation of the event sequences can be customized using the visualization tool 220 as described above.

Example User Interface

Figure 3:
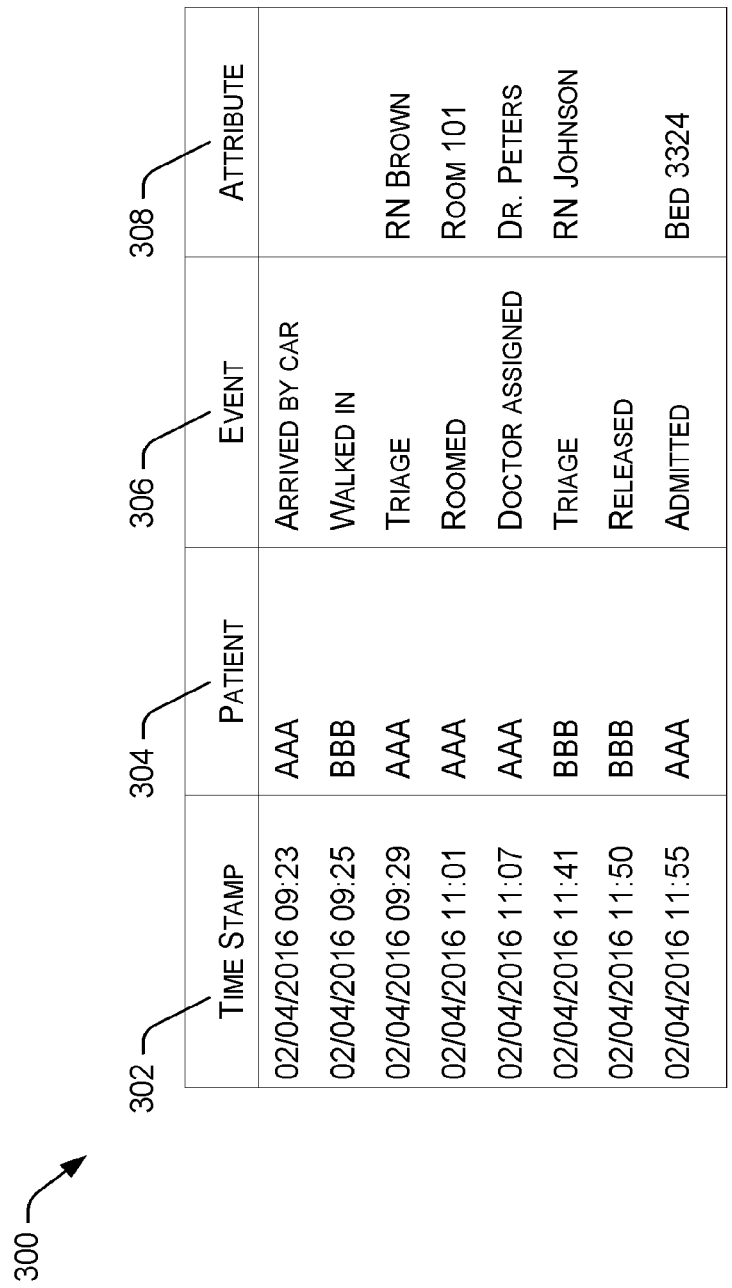
Figure 4:
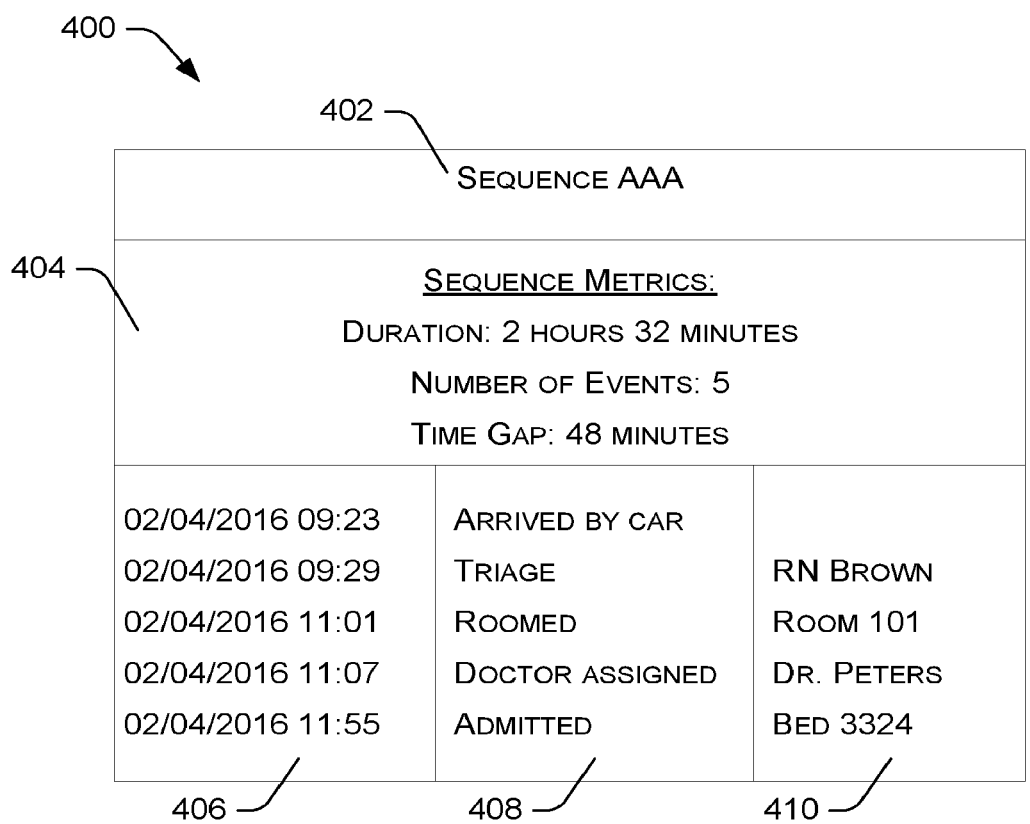
Figure 5:
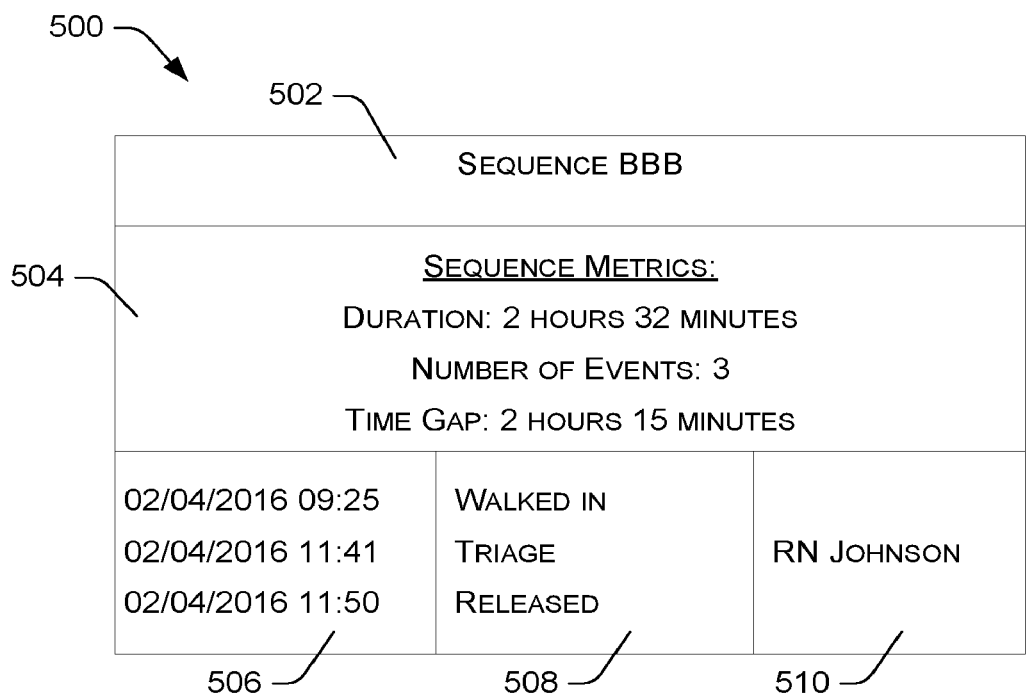

FIGS. 3 through 6 are exemplary diagrams showing how events are processed, according to one embodiment of the present invention. FIG. 3 shows a set of event sequences for triaging patients AAA and BBB. Each of the event sequences correlate to event-related data comprising a timestamp 302, a patient 304, an event description 306, and an event attribute 308. The event-related data for each specified field can be input by an end user at an end user terminal and uploaded onto the event sequencing application or imported from a database or a data source. Additionally, the event-related data can be readily updated so as to reflect any new information or correct incorrect information. In some embodiments, a set or a representative subset of event sequences can be displayed in a list format to the end user. The event sequencing application can display event sequences and metrics for all of the events in a set or for a specific group of event sequences within the set. For example, the event sequencing application can receive a filter selection to display event sequences, metrics, and/or event-related data for a particular individual. In this regard, the event sequencing application can display on the user interface event sequences 406-410 and sequence metrics 404 for a group of event-related data associated with patient AAA 402, as depicted in FIG. 4. Similarly, the event sequencing application can display on the user interface event sequences 506-510 and sequence metrics 504 for a group of event-related data associated with patient BBB 502, as depicted in FIG. 5. Additionally, the event sequencing application can display aggregated sequence metrics 600 for all of the event sequences in a set as depicted in FIG. 6.

Figure 7:
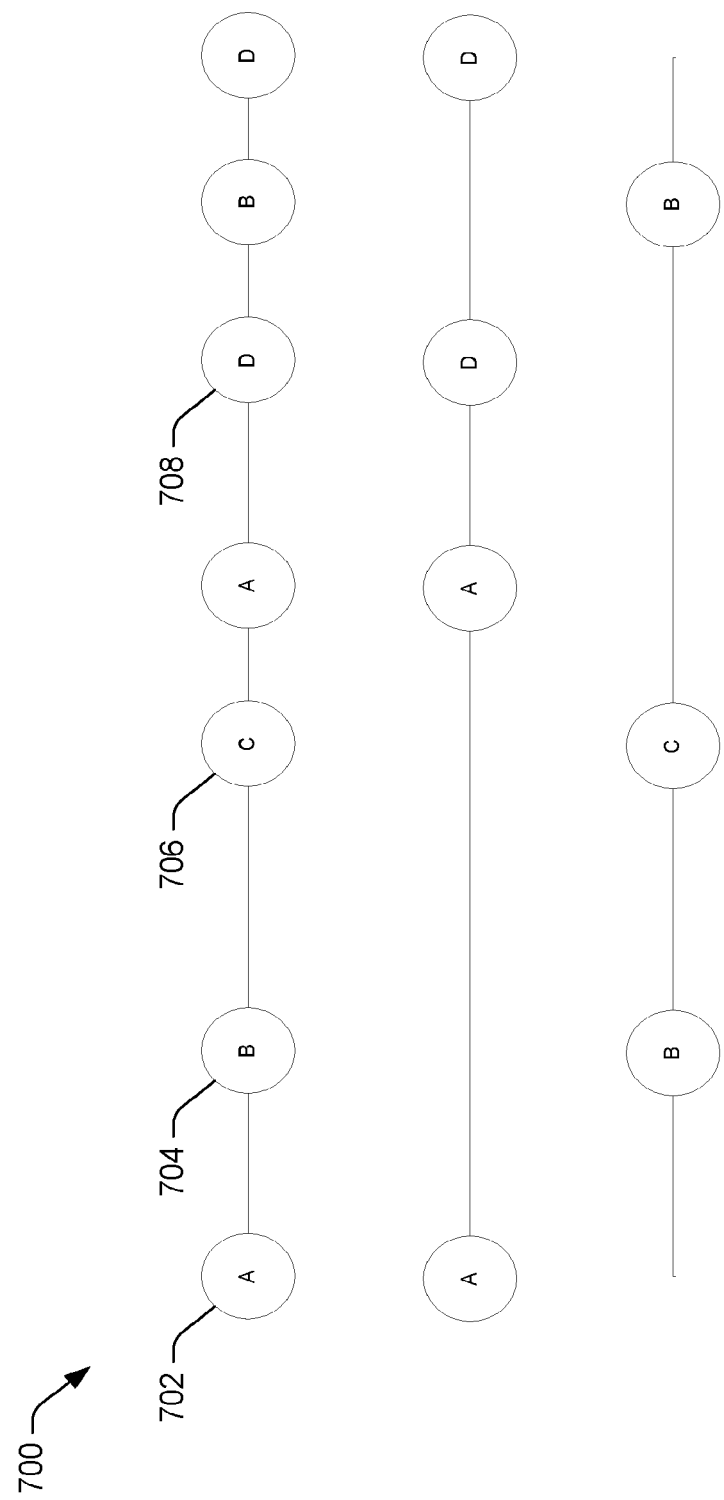
FIG. 7 shows an exemplary visual of a single event sequence as one or more parallel subsequences.

FIG. 7 shows an exemplary graphical user interface (GUI) of the application user interface comprising a visual of a single set of event sequences and one or more parallel subsequences thereof. In the illustrated embodiment, the single set of event sequences comprises four groups of events—Group A 702, Group B 704, Group C 706, and Group D 708. In addition to grouping the event records into event sequences 700, the application user interface is configured to display a single event sequence as one or more parallel subsequences. In the illustrated embodiment, the events from the single set of event sequences are separated into a first group comprising A and D events and a second group comprising B and C events such that the first parallel subsequence includes events in Groups A and D, and the second parallel subsequence includes events in Groups B and C. Breaking up the single event sequence into one or more parallel subsequences allows an end user to analyze time gap between events, frequency of events in specific event groups, and/or so forth. In various embodiments, the end user can manipulate the presentation of the subsequences by adjusting settings, selecting filters, or customizing parameters, for example, by using a visualization tool. For example, events in Groups A and B can appear in the first parallel subsequence and events in Groups C and D can appear in the second parallel subsequence.

Figure 8:
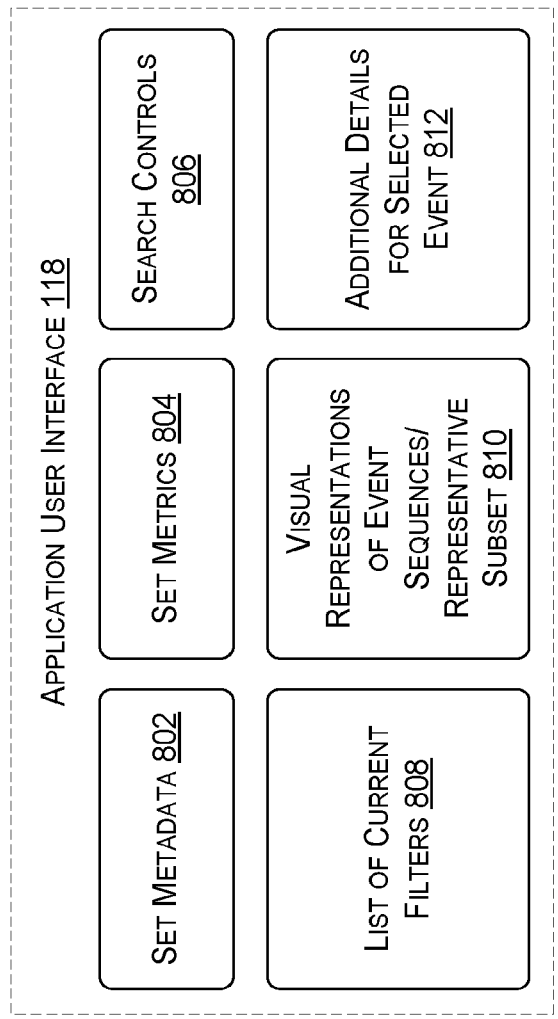
FIG. 8 shows an exemplary application user interface for displaying event sequences, set metadata, set metrics, and related information.

FIG. 8 shows an exemplary application user interface for displaying event sequences, set metadata, set metrics, and related information. The application user interface 118 is configured to interact with one or more components of the present system, for example, the event sequencing application. Without limitation, the user interface comprises various elements relating to event-related data, including: set metadata 802, which describes the current set of sequences, for example, name, number of sequences, number and percent of currently filtered sequences; set metrics 804, which can include a duration of sequences, a number of events and number of unique events per sequence, a time gap between the consecutive events, a distribution of first and last events in the sequences; search controls 806, which allows the end user to filter the timelines for the event sequences based on the metric values (e.g., time gap, number of sequences, duration, etc.) or the sequence patterns; a list of current filters 808, which allows the end user to remove one or more of the filters based on the metric values or the sequence patterns from the set; a visual representation 810 of event sequences and/or the representative subset of the sequences; and additional details of a selected event within the set 812.

The set metadata 802, the set metrics 804, and additional details for selected event 812 can be displayed in a list format, pictorial format, graphical format, chart format, and/or so forth. Similarly, the search controls 806 and the list of current filters 808 can appear in a list format, in a drop down menu, checkbox format, and/or so forth. The visual representations of event sequences and/or a representative subset of event sequences 810 can be displayed in a list format, pictorial format, graphical format, chart format, and/or so forth. Additionally, the elements 802-812 on the application user interface 118 can be customized for display. For example, an end user can drag-and-drop various elements 802-812 to different locations on the application user interface 118. Alternatively, one or more elements 802-812 can be removed or added to the application user interface. Further, each of the elements 802-812 can be manipulated using a visualization tool so as to highlight or color code certain data or information. In various embodiments, the elements 802-812 can comprise a small subset of data that is representative of the full set of data or a part of a larger set of data for providing fast and simplified visualization of event-related data. In this regard, the elements 802-812 can comprise an icon or a link that can be activated to display the full set of data or the entire dataset on the application user interface.

Example Processes

Figure 9:
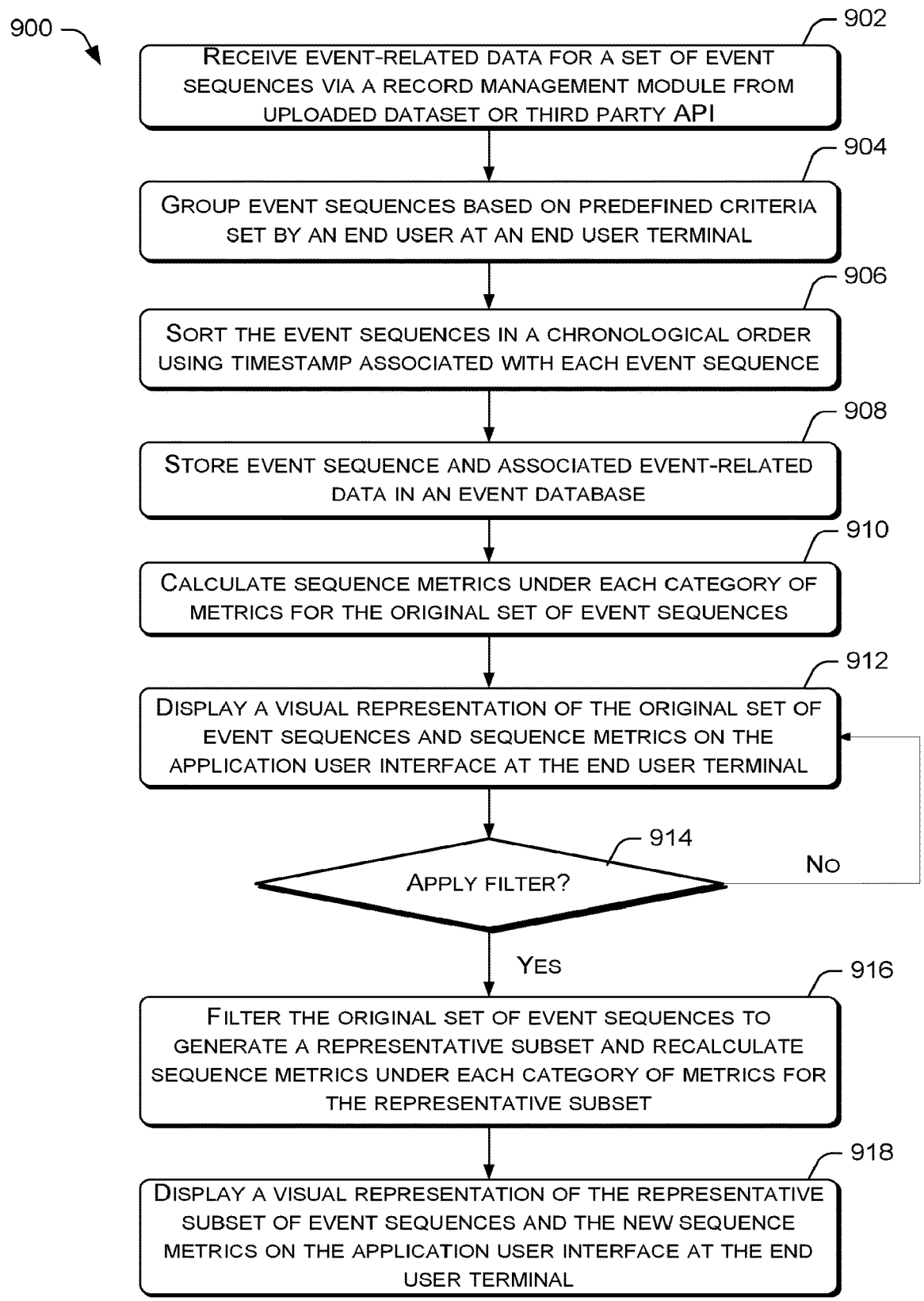
FIG. 9 is a flow diagram of an example process for visually analyzing event sequences.

FIG. 9 presents illustrative process 900 for using the event sequencing application to conduct a visual analysis of event sequences. The process 900 is illustrated as a collection of blocks in a logical flow chart, which represents a sequence of operations that can be implemented in hardware, software, or a combination thereof. In the context of software, the blocks represent computer-executable instructions that, when executed by one or more processors, perform the recited operations. Generally, computer-executable instructions may include routines, programs, objects, components, data structures, and the like that perform particular functions or implement particular abstract data types. The order in which the operations are described is not intended to be construed as a limitation, and any number of the described blocks can be combined in any order and/or in parallel to implement the process. For discussion purposes, the process 900 is described with reference to FIGS. 1 through 8.

In order to analyze the sequences, an end user uploads event-related data into the application in the form of records where each record represents an event. In some embodiments, the records could be uploaded as one or more comma-separated files. Alternatively, the record management module can request for event-related data from one or more databases or data sources. As indicated in block 902, the record management module receives event-related data from an uploaded dataset or third party API. The event-related data can be partially or wholly replicated on the record management module in order to facilitate quick access. As indicated in block 904, the event grouping module groups events based on predefined criteria that can be set by the end user at an end user terminal. Alternatively, the event grouping module can group events based on the probability of the events to occur in the same event sequence or based on machine learning algorithms. As indicated in block 906, the event sequencing module sorts the events in a chronological order. For example, the event sequencing module can sort the events at least in part based on the timestamp associated with each event (e.g., earliest event to the latest event). As indicated in block 908, the record management module stores the sorted event sequence (i.e., by groups and/or in chronological order) and associated event data in an event database.

As indicated in block 910, the sequence analysis module calculates sequence metrics under each category of metrics for the original set of event sequences. It is contemplated that each set can comprise any number of event sequences, depending upon the embodiment. Without limitation, the metrics include total time duration of a sequence, a number of events in a sequence, a number of unique events, a maximum time gap between the consecutive events, a distribution of the first events in a sequence, a distribution of the last events in a sequence, a total number of sequences in the data, and/or so forth. In this regard, the sequence analysis module analyzes event-related data for each event in the sorted event sequence in order to determine qualitative and quantitative sequence metrics. For example, the sequence analysis module analyzes the timestamp associated with each event in the event sequences in order to calculate the total time direction of a sequence and the maximum time gap between consecutive events. As indicated in block 912, the application user interface displays a visual representation of the original set of event sequences and correlating sequence metrics on the application user interface at the end user terminal. The visual representation of the event sequences can be customized using the visualization tool at the end user terminal. For example, the visualization tool enables the end user to highlight, re-order, color code, annotate, remove, and/or add event sequences.

At decision block 914, the event sequencing application can determine if any filter is applied. To apply filter ("yes" response from decision block 914), the sorting tool of the event grouping module receives a filter selection, from the end user, to filter the original set of event sequences and generate a new representative subset or a new representative sample of event sequences, as indicated in block 916. The sequence filtering can be based at least in part on the values of any sequence metrics, absence or presence of specific events, presence of the patterns of the events such as, for example, event A then event B then event C and no event D between events B and C. In various embodiments, filter can be randomly applied such that the sequences for the subset or new sample of event sequences can be selected randomly from the set. Upon applying a filter to generate a new representative subset or a new representative sample of event sequences from the original set of event sequences, the sequence analysis module recalculates the sequence metrics for the new representative subset or the new representative sample of event sequences. At block 918, application user interface displays a visual representation of the new representative subset or the new representative sample and the recalculated sequence metrics on the application user interface at the end user terminal.

CONCLUSION

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A computer-implemented method for a visual analysis of event sequences, the method comprising:
    receiving event-related data for a set of event sequences, the event-related data being received from ne or more data sources;
    selecting one or more event grouping criteria from a list of event grouping criteria, wherein the list of event grouping criteria comprises a criterion of grouping by an event location, a criterion of grouping by an event entity, and a criterion of grouping by an event time;
    grouping, into one or more groups, event sequences within the set of event sequences based on the selected event grouping criteria;
    calculating sequence metrics for each group of event sequences within the set of event sequences;
    displaying, on a user interface, the sequence metrics for the set of event sequences,
    receiving, via the user interface, a filter selection for the set of event sequences,
    generating a new representative sample subset of the set of event sequences based at least in part on the filter selection,
    recalculating sequence metrics for the new representative sample subset of the set of event sequences, and
    causing the recalculated sequence metrics for the set of event sequences to be displayed in the user interface.

2. The computer-implemented method of claim 1, further comprising:
    generating a visual representation of each group of event sequences within the set of event sequences,
    causing the visual representation of each group of event sequences within the set of event sequences to be displayed in the user interface;
    generating a new visual representation of the new representative sample subset of the set of event sequences; and
    causing the new visual representation of the new representative sample subset of the set of event sequences to be displayed in the user interface.

3. The computer-implemented method of claim 2, wherein the visual representation of the set of event sequences includes a single set of event sequences and one or more parallel subsequences of the single set of event sequences.

4. The computer-implemented method of claim 1, further comprising:
    receiving, via the user interface, a selection to modify a visual representation of the set of event sequences;
    generating a new visual representation of the set of event sequences based at least in part on the selection; and
    causing the new visual representation of the set of event sequences to be displayed in the user interface.

5. The computer-implemented method of claim 1, wherein the grouping further comprises:
    determining a probability of the events occurring in a same event sequence; and
    if the probability exceeds a probability threshold, grouping the events in the same event sequence.

6. The computer-implemented method of claim 1, wherein the sequence metrics comprises a duration of each of the event sequences, a number of events in the set of event sequences, and a time gap between consecutive event sequences.

7. The computer-implemented method of claim 1, further comprising:
    sorting the event sequences in a chronological order based at least in part on a timestamp associated with each of the event sequences.

8. A non-transitory computer-readable medium storing instructions, which when executed by a processor, cause the processor to perform operations comprising:
    receiving event-related data for a set of event sequences, the event-related data being received from ne or more data sources;

selecting ne or more event grouping criteria from a list of event grouping criteria, wherein the list of event grouping criteria comprises a criterion of grouping by an event location, a criterion of grouping by an event entity, and a criterion of grouping by an event time;
grouping, into one or more groups, event sequences within the set of event sequences based on the selected event grouping criteria;
calculating sequence metrics for each group of event sequences within the set of event sequences;
displaying, on a user interface, the sequence metrics for the set of event sequences;
receiving, via the user interface, a filter selection for the set of event sequences;
generating a new representative sample subset of the set of event sequences based at least in part on the filter selection;
recalculating sequence metrics for the new representative sample subset of the set of event sequences; and
causing the recalculated sequence metrics for the set of event sequences to be displayed in the user interface.

9. The non-transitory computer-readable medium of claim 8, the operations further comprising:
generating a visual representation of each group of event sequences within the set of event sequences;
causing the visual representation of each group of event sequences within the set of event sequences to be displayed in the user interface;
generating a new visual representation of the new representative sample subset of the set of event sequences; and
causing the new visual representation of the new representative sample subset of the set of event sequences to be displayed in the user interface.

10. The non-transitory computer-readable medium of claim 9, wherein the visual representation of the set of event sequences includes a single set of event sequences and one or more parallel subsequences of the single set of event sequences.

11. The non-transitory computer-readable medium of claim 8, the operations further comprising:
receiving, via the user interface, a selection to modify a visual representation of the set of event sequences;
generating a new visual representation of the set of event sequences based at least in part on the selection; and
causing the new visual representation of the set of event sequences to be displayed in the user interface.

12. The non-transitory computer-readable medium of claim 8, wherein the grouping further comprises:
determining a probability of the events occurring in a same event sequence; and
if the probability exceeds a probability threshold, grouping the events in the same event sequence.

13. The non-transitory computer-readable medium of claim 8, wherein the sequence metrics comprises a duration of each of the event sequences, a number of events in the set of event sequences, and a time gap between consecutive event sequences.

14. The non-transitory computer-readable medium of claim 8, the operations further comprising:
sorting the event sequences in a chronological order based at least in part on a timestamp associated with each of the event sequences.

15. A system for a visual analysis of event sequences, the system comprising:
a memory; and
a processor, coupled to the memory, to perform operations comprising:
receiving event-related data for a set of event sequences, the event-related data being received from one or more data sources;
selecting one or more event grouping criteria from a list of event grouping criteria, wherein the list of event grouping criteria comprises a criterion of grouping by an event location, a criterion of grouping by an event entity, and a criterion of grouping by an event time;
grouping, into one or more groups, event sequences within the set of event sequences based on the selected event grouping criteria;
calculating sequence metrics for each group of event sequences within the set of event sequences;
displaying, on a user interface, the sequence metrics for the set of event sequences;
receiving, via the user interface, a filter selection for the set of event sequences;
generating a new representative sample subset of the set of event sequences based at least in part on the filter selection;
recalculating sequence metrics for the new representative sample subset of the set of event sequences, and
causing the recalculated sequence metrics for the set of event sequences to be displayed in the user interface.

16. The system of claim 15, the operations further comprising:
generating a visual representation of each group of event sequences within the set of event sequences;
causing the visual representation of each group of event sequences within the set of event sequences to be displayed in the user interface;
generating a new visual representation of the new representative sample subset of the set of event sequences; and
causing the new visual representation of the new representative sample subset of the set of event sequences to be displayed in the user interface.

17. The system of claim 16, wherein the visual representation of the set of event sequences includes a single set of event sequences and one or more parallel subsequences of the single set of event sequences.

18. The system of claim 15, the operations further comprising:
receiving, via the user interface, a selection to modify a visual representation of the set of event sequences;
generating a new visual representation of the set of event sequences based at least in part on the selection; and
causing the new visual representation of the set of event sequences to be displayed in the user interface.

19. The system of claim 15, wherein the grouping further comprises:
determining a probability of the events occurring in a same event sequence; and
if the probability exceeds a probability threshold, grouping the events in the same event sequence.

20. The system of claim 15, wherein the sequence metrics comprises a duration of each of the event sequences, a number of events in the set of event sequences, and a time gap between consecutive event sequences.

* * * * *